United States Patent
Liphardt et al.

(10) Patent No.: US 7,567,345 B1
(45) Date of Patent: Jul. 28, 2009

(54) ELLIPSOMETER MEETING SCHEIMPFLUG CONDITION WITH PROVISION OF AN ESSENTIALLY CIRCULAR ELECTROMAGNETIC RADIATION SPOT ON A SAMPLE

(75) Inventors: Martin M. Liphardt, Lincoln, NE (US); Brooks A. Hitt, Lincoln, NE (US); Jeffrey S. Hale, Lincoln, NE (US); Ping He, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 366 days.

(21) Appl. No.: 11/784,750

(22) Filed: Apr. 10, 2007

Related U.S. Application Data (60) Provisional application No. 60/878,799, filed on Jan. 5, 2007.

(51) Int. Cl.
*G01J 4/00* (2006.01)

(52) U.S. Cl. .................................. 356/369; 356/364
(58) Field of Classification Search .......... 356/364–369
See application file for complete search history.

(56) References Cited

U.S. PATENT DOCUMENTS

| | | | |
|---|---|---|---|
| 5,517,312 A | 5/1996 | Finarov | 356/630 |
| 5,963,326 A | 10/1999 | Masao | 356/369 |
| 6,028,671 A * | 2/2000 | Svetkoff et al. | 356/368 |
| 6,897,955 B2 | 5/2005 | Wielsch | 356/369 |
| 7,095,498 B2 | 8/2006 | Horie et al. | 356/364 |
| 7,245,375 B2 * | 7/2007 | Finarov | 356/364 |

* cited by examiner

*Primary Examiner*—L. G Lauchman
(74) *Attorney, Agent, or Firm*—James D. Welch (57) ABSTRACT

A reflectometer, ellipsometer, polarimeter or the like system with aperture, focusing means, sample and optionally detector planes oriented so that the Scheimpflug condition is substantially met on incident and/or, optionally, reflection sides of a sample. In addition beneficial aperture hole aspect ratio and aperture plane orientation is described.

14 Claims, 7 Drawing Sheets

ELLIPSOMETER MEETING SCHEIMPFLUG CONDITION WITH PROVISION OF AN ESSENTIALLY CIRCULAR ELECTROMAGNETIC RADIATION SPOT ON A SAMPLE

This Application Claims Benefit of Provisional Application Ser. No. 60/878,799 Filed Jan. 5, 2007.

TECHNICAL FIELD

The present invention relates to reflectometer, ellipsometer, polarimeter or the like systems, and more particularly is a system with aperture, focusing means and sample planes, and optionally sample, second focusing means and detector oriented so that the Scheimpflug condition is substantially met. In addition beneficial aperture hole aspect ratio conditions, in combination with aperture plane orientation, are described.

BACKGROUND

It is known to provide cameras which are designed so that the Scheimpflug condition is substantially met to enable providing an image to a film which is in focus over a large film area even though the source of the image is spatially distributed over varying distances from the camera lens. It is also known that when a beam of electromagnetic radiation is directed to a sample at an oblique angle of incidence, if, for instance it is essentially circular at the source thereof, then it appears as an ellipse at a sample surface. The shape of the spot on the sample can be modified by providing an elliptically shaped aperture at the source, or alternatively, by rotating an aperture with a circular hole therein to appear to the beam as an ellipse or some combination thereof. Properly orienting such an aperture will preshape the source beam so that when it impinges on the sample an essentially circular spot is achieved.

A Patent to Horie, U.S. Pat. No. 7,095,498 describes the presence of a pinhole mirror in a spectroscopic ellipsometer system. The pinhole mirror is rotated so that a beam of electromagnetic radiation is oriented along a locus which is oblique angle, rather than along a normal thereto.

A Patent to Masao, U.S. Pat. No. 5,963,326 describes an imaging ellipsometer which uses a large cross-section measuring beam rather than a small beam spot as is the focus in the present invention.

A Patent to Finarov, U.S. Pat. No. 5,517,312 mentions the Scheimpflug condition in the context of a scanning ellipsometer wherein a beam is scanned over a sample and a pattern recognition camera which is designed to utilize the Scheimpflug condition is applied.

Also disclosed is a Patent to Wielsch, U.S. Pat. No. 6,897,955 and related Application PCT WO01/86257 and Patent DE 10023411 which describe a rectangular aperture opening to make a square measurement spot. The opening is adjustable in size and geometry but there is not mention of tilting the aperture.

The prior art does not, to the Inventor's knowledge, describe applying the Scheimpflug condition to design of reflectometer, ellipsometer, polarimeter or the like systems, especially when combined with tailoring the shape of an aperture to provide a sharply focused circular spot at a sample when it is oriented as require to meet the Scheimpflug condition.

Need exists for improved a system and method of providing electromagnetic radiation to a sample and/or detector wherein focus is achieved over substantially the entire area of a spot of electromagnetic radiation impinging thereupon.

DISCLOSURE OF THE INVENTION

In its basic embodiment the present invention comprises:
a) a source of a beam of electromagnetic radiation;
b) an aperture with a hole therethrough;
c) a focusing means; and
d) a stage for supporting a sample.

To form an ellipsometer or polarimeter the system requires additional components such as a detector, and polarization setting and monitoring elements such as a polarizer, an analyzer and perhaps one or more compensators. However, for the purposes of disclosing the present invention there is no need to involve said other components. (It is noted that where the polarizer and analyzer are absent the system can comprise a reflectometer).

While all reflectometer, ellipsometer, polarizer or the like systems can be described as comprising the identified components, a present invention novel aspect is found in orientating and positioning identified elements such that the "Scheimpflug" condition is substantially met. To meet this condition in use, said source of a beam of electromagnetic radiation is caused to direct a beam of electromagnetic radiation to a sample along an oblique angle of incidence. Said locus beam approaches said focusing means along a locus which is substantially perpendicular to the plane thereof and then passes through said focusing means and impinges upon a sample placed on said stage for supporting a sample, at an angle of incidence ($\beta$) with respect to a normal to a surface of said sample. Further, the aperture is rotated such that the beam locus is oriented at an angle ($\alpha$) with respect to a perpendicular to said plane of the aperture.

Novelty is found in the requirement, for instance, that the aperture, focusing means and stage for supporting a sample be oriented with respect to one another such that a projected plane of the aperture, a projected plane of the sample surface and a projected plane of the focusing means intersect, and such that the following condition is substantially met:

$$\mathrm{Tan}(\alpha) = (X-f)/f\,\mathrm{Tan}(\beta);$$

where "X" is the distance from the aperture, at the point at which said beam passes therethrough, to a center of said focusing means, and "f" is the focal length of said focusing means.

In the foregoing the terminology "plane of the aperture" refers to a surface of the aperture orientation. That is the aperture is of a flat "sheet-like" construction through which is a hole. The exact outer shape of the aperture is not important, (it can be square, rectangular, circular or elliptical etc.). The orientation of said surface of said aperture constitutes its "plane". Further, to define the "plane" of the focusing means, consider that the focusing means can be considered to be a converging lens with a relatively long longitudinal and a relatively small lateral dimension. The "plane" of said lens is along the longitudinal direction. Another way to express this condition is that the "plane" of the focusing means is perpendicular to the Optical axis thereof. This should not be considered to limit the focusing means to being a converging lens, and mathematical equivalents using reflective optics can also be applied within the scope of the present invention.

A method of providing an oblique angle of incidence incident beam of electromagnetic radiation to a spot on a sample, wherein said beam is in focus over a substantial area of said spot comprises the steps of:

a) providing a reflectometer, ellipsometer, polarimeter or the like system as just described; and b) adjusting the orientations of said aperture, focusing means and stage for supporting a sample with respect to one another such that a projected plane of the aperture, a projected plane of the sample surface and a projected plane of the focusing means intersect along a common line, and such that the following condition is substantially met:

$$\mathrm{Tan}(\alpha) = (X-f)/f\, \mathrm{Tan}(\beta).$$

Continuing, while orienting an aperture with a hole therethrough, a focusing means and a stage for supporting a sample as described in the foregoing an in the foregoing is believed to be new, novel and non-obvious in the context of ellipsometer or the like systems, the present invention further, a preferred embodiment provides that the aperture have an aspect ratio of (x/y) and be oriented such that the locus of said beam passing through the hole in said aperture is oriented at the angle ($\alpha$) with respect to a perpendicular the plane of said aperture. The result is that the beam provides a spot on said sample with an aspect ratio of (x'/y') and the following condition is substantially met:

$$(x/y)\cos(\alpha) = (x'/y')\cos(\beta).$$

A preferred condition results where said aperture has an aspect ratio of (x/y) and is oriented such that the spot shape on the surface of the sample is substantially of unity aspect ratio, (ie. x'=y'). It is believed that the use of a non-mirrored aperture having an aspect ratio of (x/y) and which is oriented such that the locus of said beam passing through the hole in said aperture is at the angle ($\alpha$) with respect to a perpendicular the plane of said aperture, is new and novel on its own where applied to reflectometer ellipsometer, polarimeter systems. It is believed that, as opposed to using apertures with holes therethrough of non-unity aspect ratio, tilting/rotating an aperture having a hole therethrough of any aspect ratio to cause said hole to appear as an effective non-unity aspect ratio hole to the beam of electromagnetic radiation, such that a substantially unity aspect ratio spot on a sample is formed, is also new, novel, non-obvious. This is believed to be particularly true where the use of said "tipped" aperture is combined with the requirement that the Scheimpflug condition be met such that a specific aperture hole aspect ratio and orientation used results in a beam spot on a sample being made to be circular, with every point therein being in focus.

The above recital has been directed to describing a system on a source side of a sample. The "Scheimpflug" condition can also be applied to the detector-side of a system. Consider a reflectometer, ellipsometer, polarimeter or the like system comprising:

a) a source of a beam of electromagnetic radiation;
b) a stage for supporting a sample;
c) a focusing means; and
d) a detector;

wherein each of said detector, focusing means and sample are oriented in identifiable planes. In use said source of a beam of electromagnetic radiation is caused to direct a beam of electromagnetic radiation to a sample placed on said stage for supporting a sample, at an oblique angle of incidence ($\beta$) with respect to a normal to a surface of said sample and said beam reflects therefrom. The focusing means is caused to be oriented with respect to the locus of said reflected beam so that said beam approaches it substantially perpendicular to the plane of said focusing means, such that said beam passes through said focusing means and impinges upon said detector at an angle ($\alpha'$) with respect to a normal thereto. The "Scheimpflug" condition is substantially met when said detector, focusing means and stage for supporting a sample being oriented with respect to one another such that a projected plane of the detector, a projected plane of the sample surface and a projected plane of the focusing means intersect, and such that the following condition is substantially met:

$$\mathrm{Tan}(\alpha') = (X-f)/f\, \mathrm{Tan}(\beta');$$

where "X" is the distance from the detector, at the point at which said beam impinges thereupon, to a center of said focusing means, and "f" is the focal length of said focusing means.

A method of providing a reflected oblique angle of incidence incident beam of electromagnetic radiation from a spot on a sample, to a detector, wherein said reflected beam is in focus over a substantial area of a spot over which said beam impinges on said detector comprising the steps of:

a) providing a reflectometer, ellipsometer, polarimeter or the like system as just described; and b) adjusting the orientations of said stage for supporting a sample, said focusing means and said detector with respect to one another such that a projected plane of the detector, a projected plane of the sample surface and a projected plane of the focusing means intersect along a line, and such that the following condition is substantially met:

$$\mathrm{Tan}(\alpha') = (X-f)/f\, \mathrm{Tan}(\beta').$$

A reflectometer, ellipsometer, polarimeter or the like system can be designed to apply the "Scheimpflug" condition on both incident and reflection sides of a sample. Where this is done the system can comprise:

a) a source of a beam of electromagnetic radiation;
b) an aperture with a hole therethrough;
c) a first focusing means;
d) a stage for supporting a sample;
e) a second focusing means; and
f) a detector;

each of said aperture, first focusing means and sample being oriented in identifiable planes. In use said source of a beam of electromagnetic radiation is caused to direct a beam of electromagnetic radiation to a sample along an oblique angle of incidence thereto, said locus being oriented substantially perpendicular to the plane of said first focusing means such that said beam passes through said first focusing means and impinges upon a sample placed on said stage for supporting a sample, at an oblique angle of incidence ($\beta$) with respect to a normal to a surface of said sample and reflects therefrom at an angle of reflection ($\beta'$), and the locus of the incident electromagnetic beam forms an angle ($\alpha$) with respect to a normal to the plane of said aperture. Said aperture, first focusing means and stage for supporting a sample are oriented with respect to one another such that a projected plane of the aperture, a projected plane of the sample surface and a projected plane of the first focusing means intersect, and such that the following condition is substantially met:

$$\mathrm{Tan}(\alpha) = (X-f)/f\, \mathrm{Tan}(\beta);$$

where "X" is the distance from the aperture, at the point at which said beam passes therethrough, to a center of said first focusing means, and "f" is the focal length of said first focusing means. Further, each of said detector, second focusing means and sample can be oriented in identifiable planes such that in use said the locus of said reflected beam is oriented substantially perpendicular to the plane of said second focusing means such that said beam passes through said second focusing means and impinges upon said detector at an angle (α') with respect to a normal thereto, and said detector, second focusing means and stage for supporting a sample are oriented with respect to one another such that a projected plane of the detector, a projected plane of the sample surface and a projected plane of the second focusing means intersect, and such that the following condition is substantially met:

$$\mathrm{Tan}(\alpha')=(X-f)/f\,\mathrm{Tan}(\beta');$$

where "X" is the distance from the detector, at the point at which said beam impinges thereupon, to a center of said second focusing means, and "f" is the focal length of said second focusing means. Such a system provides that a beam impinges on both a sample surface, and on a detector, in focus over the area of a spot formed thereupon by the beam incident thereupon.

A method of providing an oblique angle of incidence incident beam of electromagnetic radiation to a spot on a sample, wherein said beam is in focus over a substantial area of said spot, and of providing a reflected oblique angle of incidence incident beam of electromagnetic radiation from a spot on a sample, to a detector, wherein said reflected beam is in focus over a substantial area of a spot over which said beam impinges on said detector, comprises the steps of:

a) providing a reflectometer, ellipsometer, polarimeter or the like system as just described; and b) adjusting the orientations of said aperture, first focusing means and stage for supporting a sample with respect to one another such that a projected plane of the aperture, a projected plane of the sample surface and a projected plane of the focusing means intersect along a line, and such that the following condition is substantially met:

$$\mathrm{Tan}(\alpha)=(X-f)/f\,\mathrm{Tan}(\beta);$$

and b') adjusting the orientations of said second focusing means and said detector with respect to one another such that a projected plane of the detector, a projected plane of the sample surface and a projected plane of the focusing means intersect along a line, and such that the following condition is substantially met:

$$\mathrm{Tan}(\alpha')=(X'-f)/f\,\mathrm{Tan}(\beta').$$

Figure 6:
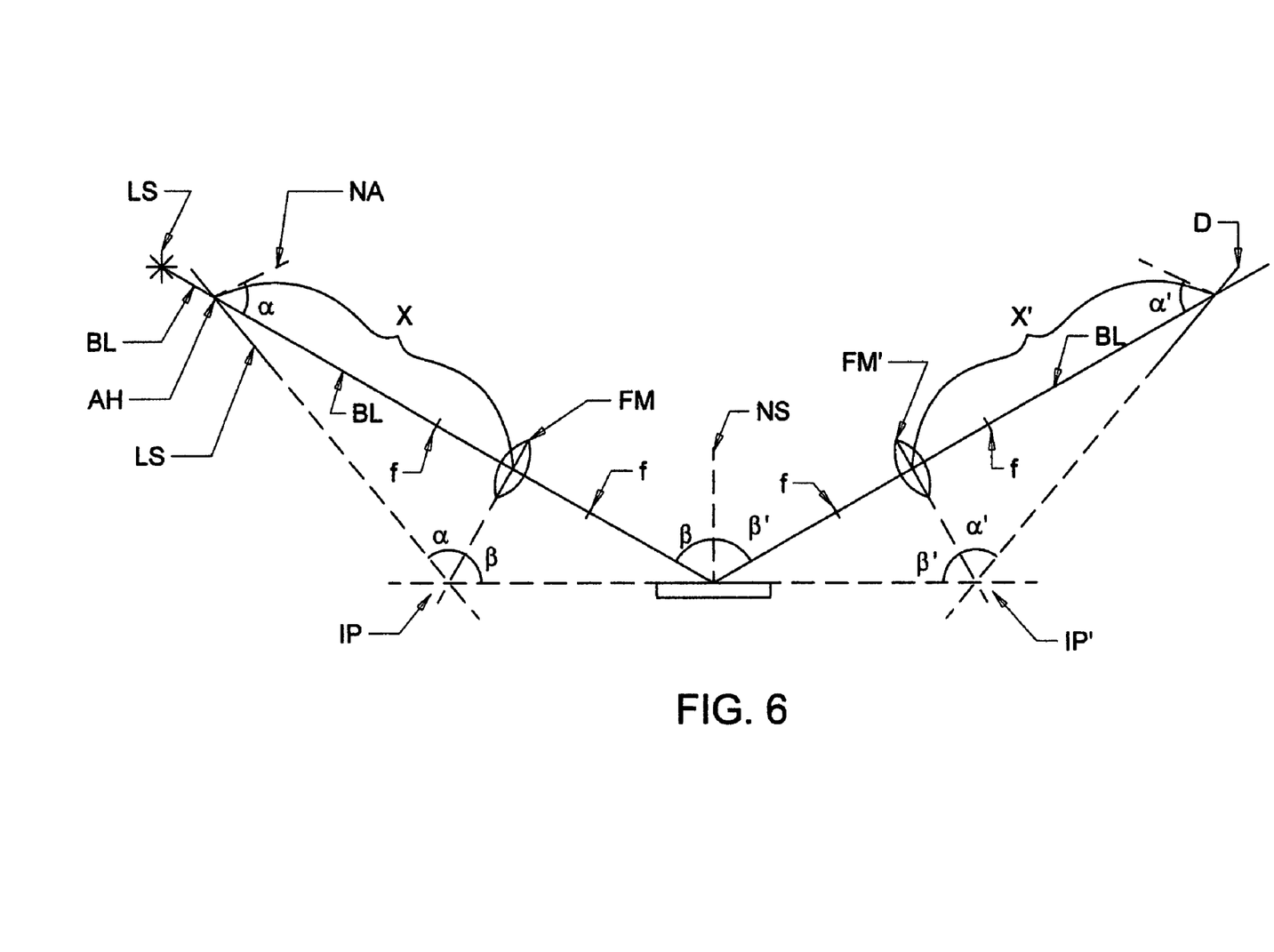
FIG. 6 shows a system wherein the "Scheimpflug" condition is substantially met on both source and detector sides of a sample.

It is noted that because a beam of electromagnetic radiation which reflects from a sample surface does so such that the angle-of-incidence (β)=angle-of-reflection (β'), in FIG. 6 the angle (β)=the angle (β').

Any of said methods can also involve using the resulting system to acquire data by causing said source of a beam of electromagnetic radiation to provide a beam to said sample and monitoring output from said detector, and performing at least one selection from the group consisting of:

storing at least some data provided by said data detector in machine readable media;

analyzing at least some of the data provided by said data detector and storing at least some of the results of said analysis in machine readable media;

displaying at least some data provided by said data detector by electronic and/or non-electronic means;

analyzing at least some of the data provided by said data detector and displaying at least some of the results of said analysis by electronic and/or non-electronic means;

causing at least some data provided by said data detector to produce a signal which is applied to provide a concrete and tangible result;

analyzing at least some of the data provided by said data detector and causing at least some thereof to produce a signal which is applied to provide a concrete and tangible result.

The present invention will be better understood by reference to the Detailed Description Section of this Specification, with reference to the Drawings.

DETAILED DESCRIPTION

Figure 1:
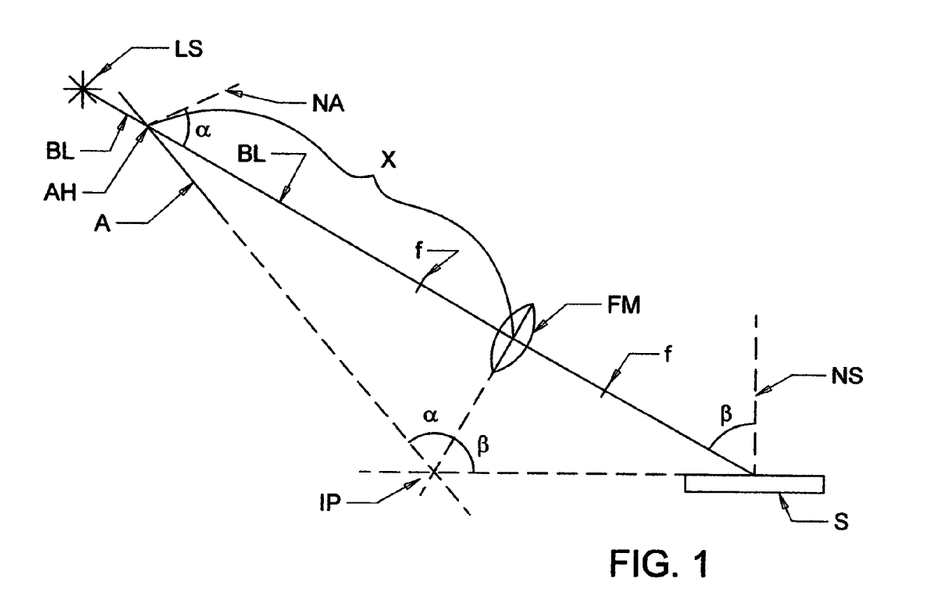
FIG. 1 shows relative positioning and orientation of a beam of electromagnetic radiation, an aperture, a focusing means, (eg. lens), and a sample and a mathematical relationship defined by the "Scheimpflug" condition.

Turning now to the Drawings, there are shown in FIG. 1 relative positioning and orientation of the locus of a Beam of electromagnetic radiation (BL) from a Source (LS) thereof, and a projected normal (NA) to the plane of the Aperture (A), a Focusing Means (FM), (eg. lens), and a Sample (S) and a mathematical relationship defined by the "Scheimpflug" condition. Note the location of the identified elements and how the angles (α) and (β) are defined. In particular, Alpha (α) is the angle between the Beam (BL) and a normal to the plane of the Aperture (A), and Beta (β) is the oblique angle between said Beam (BL) and a normal to the plane of the Sample (S). The Equation shown is the defining equation for the Scheimpflug condition:

$$\mathrm{Tan}(\alpha)=(X-f)/f\,\mathrm{Tan}(\beta);$$

where "X" is the distance from the aperture, at the point at which said beam passes therethrough, to a center of said focusing means, and "f" is the focal length of said focusing means. Again, Alpha (α) is the angle of rotation of the Perpendicular to the plane of the Aperture (A) with respect to the Beam (BL), and Beta (β) is the oblique angle of incidence of the beam on the Sample (S) surface. Note that projected planes of the Aperture (A), Focusing Means (FM) and Sample (S) intersect at Intersection Point (IP) when the Scheimpflug condition is substantially met.

Figure 2A:
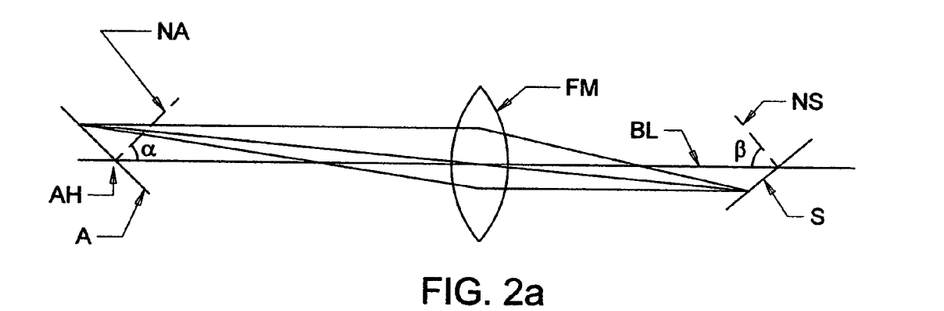
FIG. 2a shows a relationship between the orientation of an aperture and a sample, such that knowing the aspect ratio of a hole through the aperture allows determining the aspect ratio of a spot which appears on a sample.

FIG. 2a shows a relationship between the orientation of an Aperture (A) and a Sample (S), such that knowing the Aspect ratio (x/y) of a Hole (AH) through the Aperture (A) allows determining the Aspect ratio (x'/y') of a Spot (SS) which appears on a Sample (S). Note that a circular Aperture through which a beam of electromagnetic radiation, directed along a normal to a plane of said aperture passes, results in an elliptical spot shape on a sample where the beam angle-of-incidence is oblique. Also indicated are that an Aperture hole (AH) aspect ratio of 1.4 can provide a Circular spot (SS) on a Sample (S) oriented at a 45 degree angle of incidence. The defining equation which relates Input Aspect Ratio (IAR), (ie. x/y), Angle of Incidence (AOI), (ie. ($\beta$)), and ($\alpha$) is:

$$IAR \times \cos(\alpha) = OAR \times \cos(\beta); \text{ or}$$

$$(x/y) \times \cos(\alpha) = (x'/y') \cos(\beta).$$

Figure 2B:
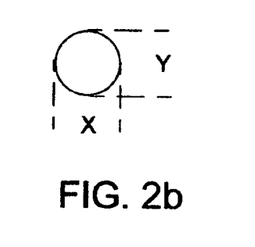
FIGS. 2b and 2c demonstrate aperture aspect ratios.
Figure 2C:
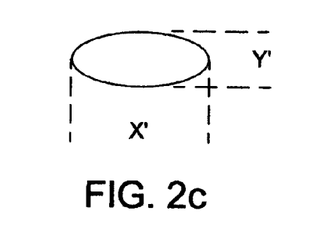

FIGS. 2b and 2c demonstrate the (x/y and (x'/y') aperture aspect ratios.

Figure 3A:
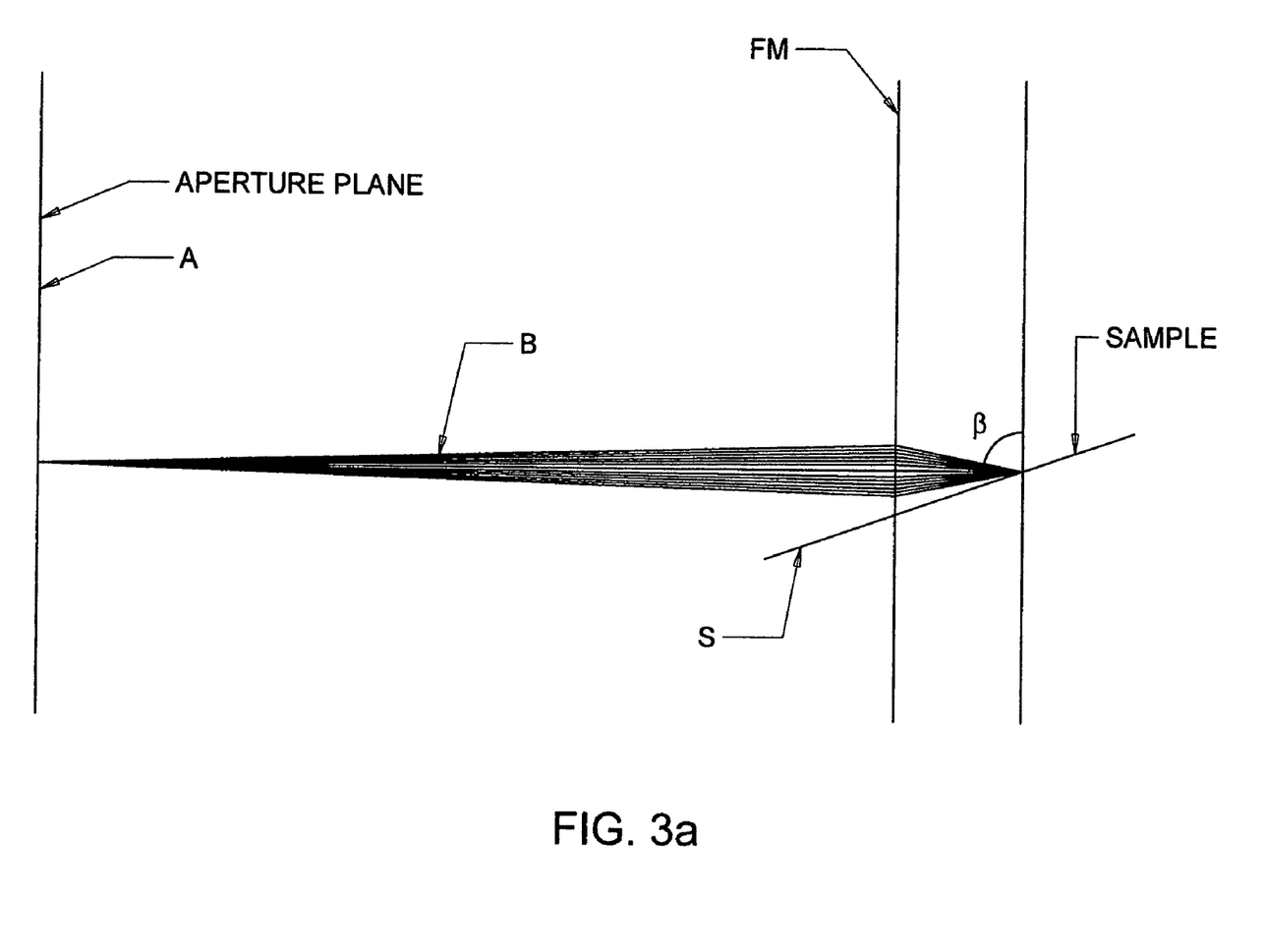
FIG. 3a shows a large scale beam diagram for a beam passing through a hole in an aperture, the plane of which is oriented at 90 degrees to said beam.
Figure 3B:
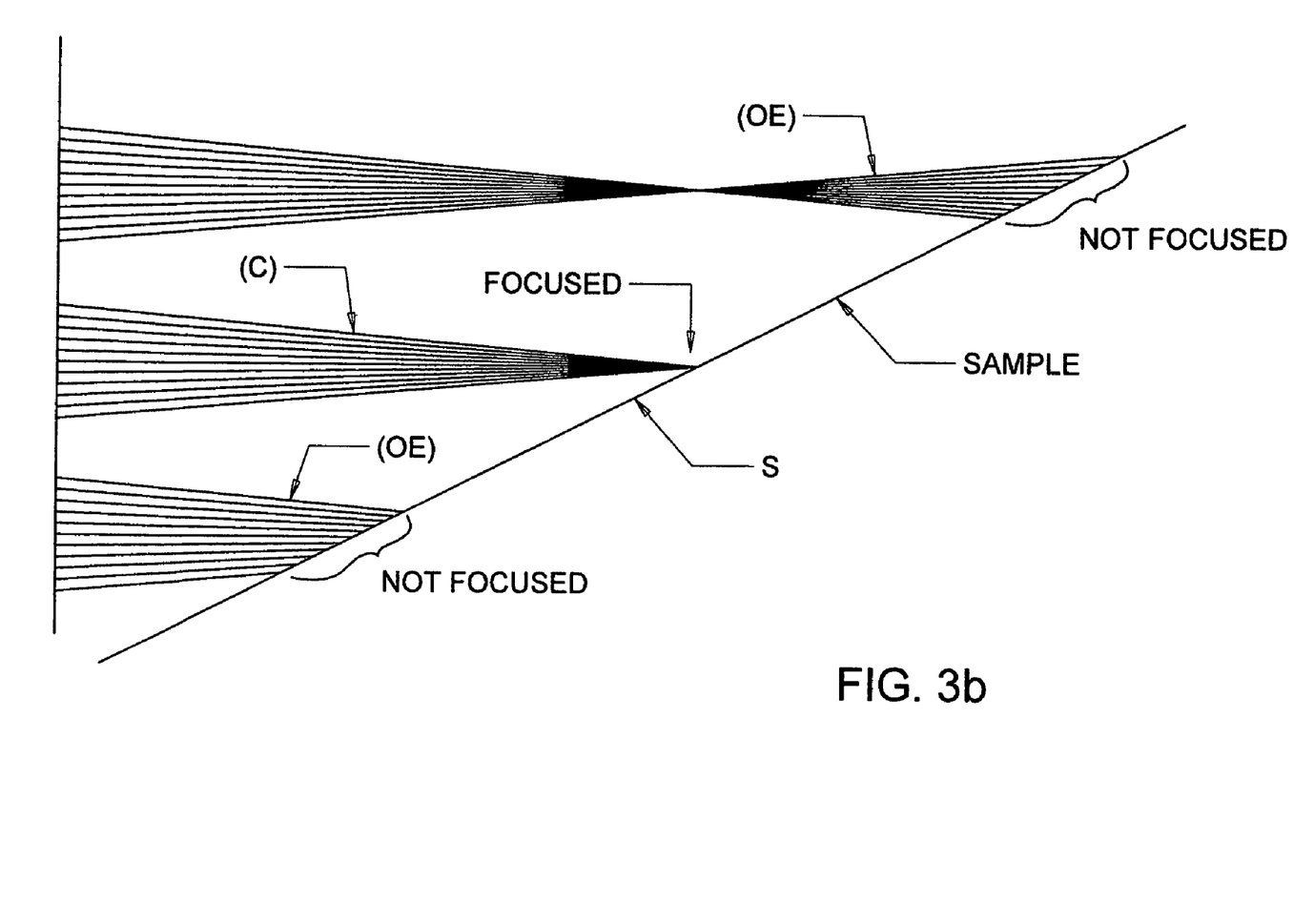
FIG. 3b shows the condition of FIG. 3a in a magnified area near the sample.

FIG. 3a shows a large scale beam diagram for a beam passing through a hole in an Aperture (A), the plane of which is oriented at 90 degrees to said beam. Note that the Beam (B) approaches the Sample (S) along an Angle of Incidence (AOI) of ($\beta$) as it exits the Focusing Means (FM). FIG. 3b shows the condition of FIG. 3a in a magnified area near the Sample (S). Note beam components (C) from near the center thereof are focused. These originate near the center of the Aperture (A) in FIG. 3a. However, the beam components (OE) that originate from near the edge of the Hole (AH) in the Aperture (A) are not in focus. This effect lead to a fuzzy spot on the Sample (S).

Figure 4A:
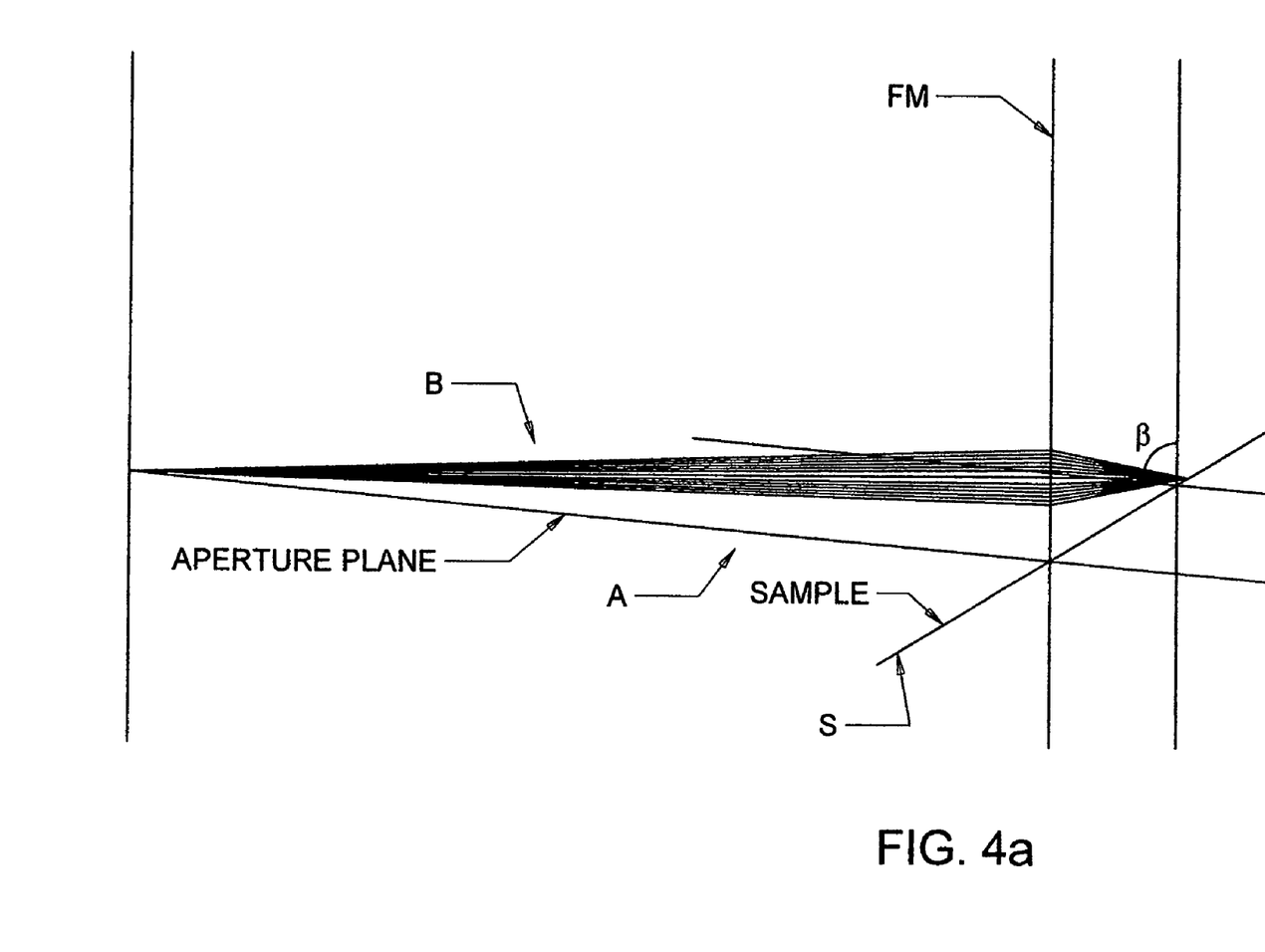
FIG. 4a shows a large scale beam diagram for a beam passing through a hole in an aperture, the plane of which is oriented at and angle offset from 90 degrees to said beam.
Figure 4B:
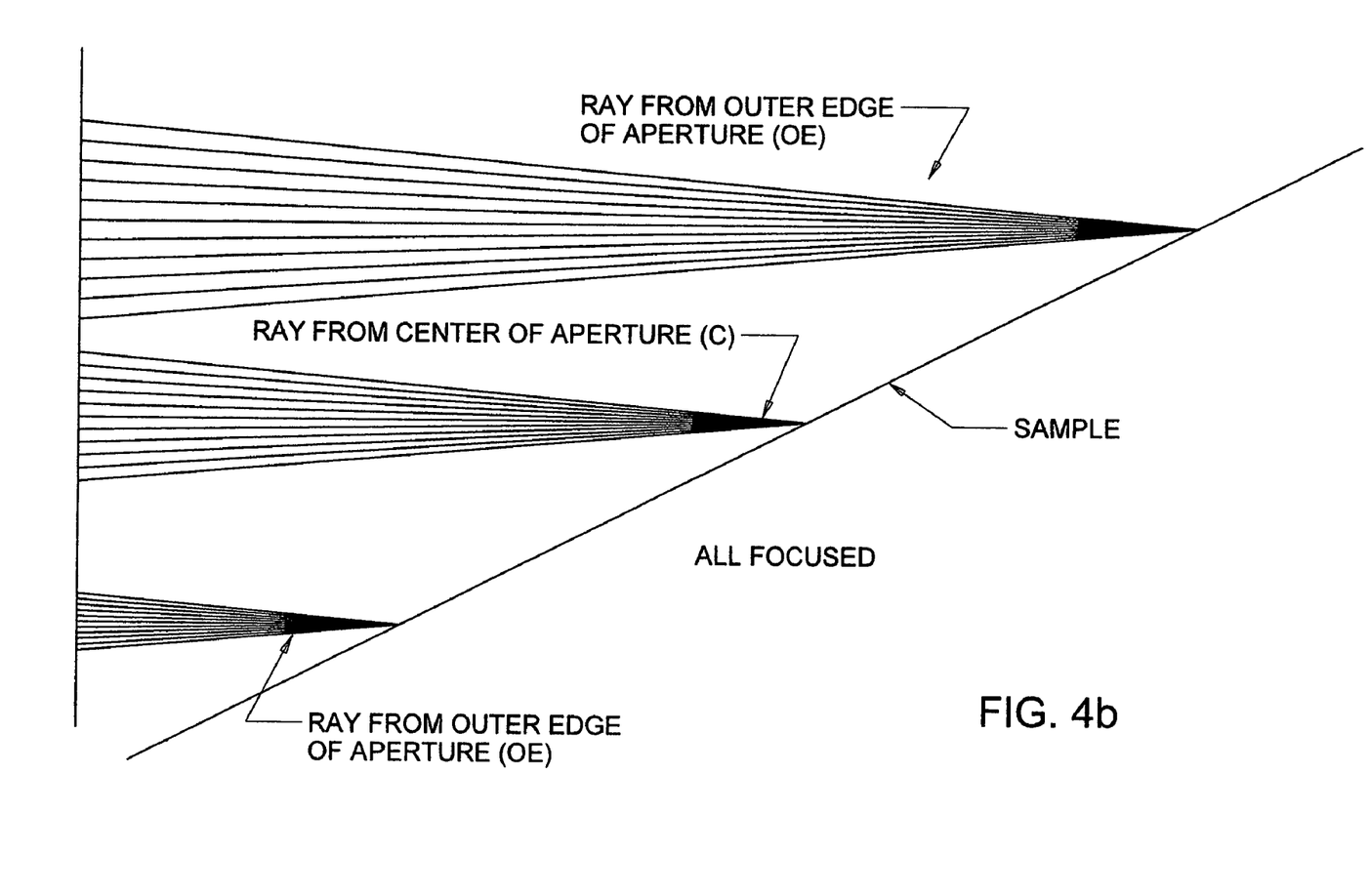
FIG. 4b shows the condition of FIG. 4a in a magnified area near the sample.

FIG. 4a shows a large scale beam diagram for a beam passing through a hole in an Aperture (A), the plane of which is oriented at and angle offset from 90 degrees to said Beam (B). As with respect to FIG. 3a, the beam impinges on the Sample (S) along an Angle of Incidence (AOI) of ($\beta$) as it exits the Focusing Means (FM). Like FIG. 3b, FIG. 4b shows the condition of FIG. 4a in a magnified area near the Sample (S). Note however, that all components (OE) and (C) of the Beam (B) are in focus at the Sample (S). This is the benefit provided by meeting the Scheimpflug condition.

Figure 5:
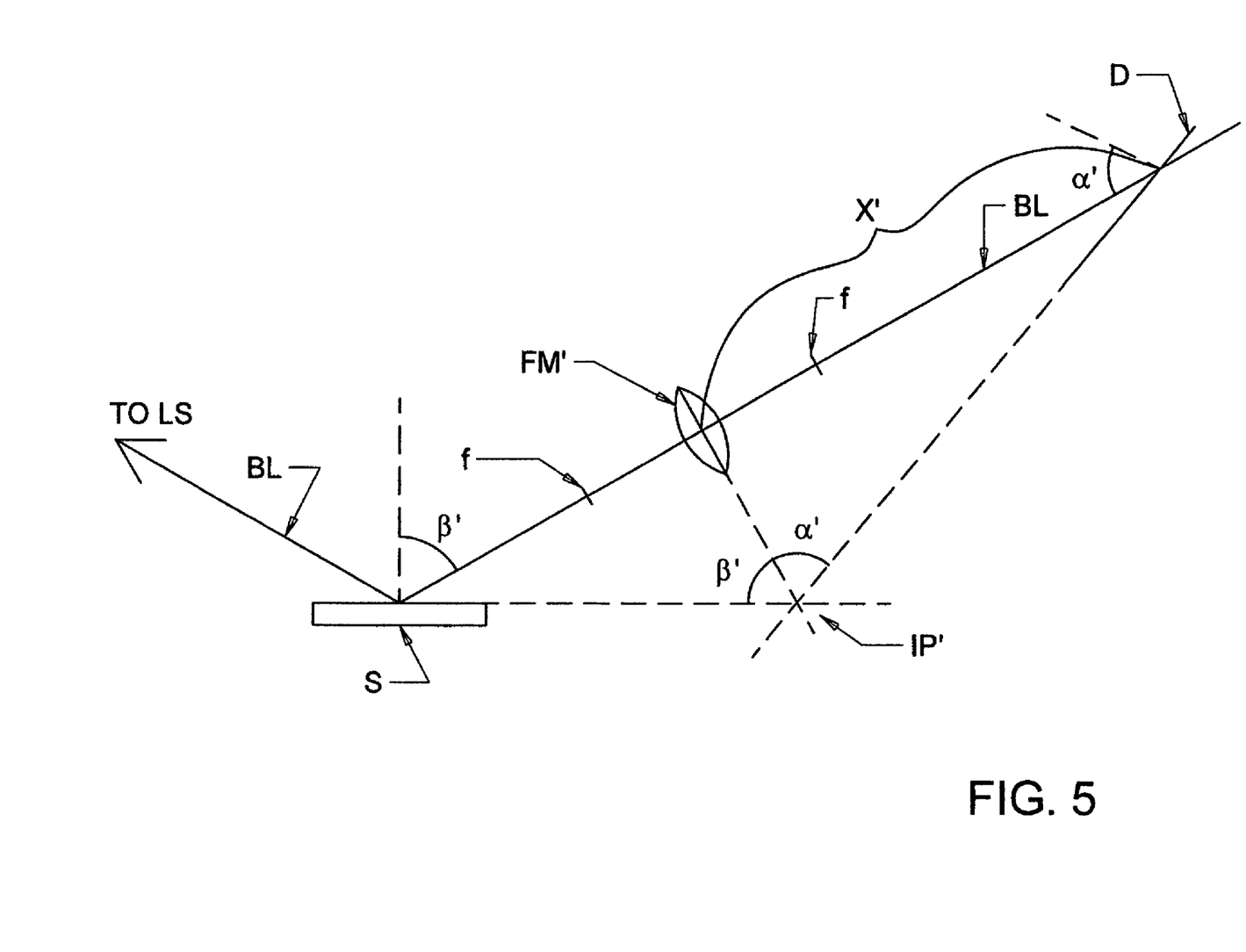
FIG. 5 shows the "Scheimpflug" condition, as demonstrated on the source side in FIG. 1, applied to the detector side of a system.

FIG. 5 shows the "Scheimpflug" condition, as demonstrated on the source side in FIG. 1, applied to the Detector side of a Sample (S). Note that the planes of the Sample (S), Detector (D) and Focusing Means (FM) intersect along a line at (IP').

FIG. 6 shows a system wherein the "Scheimpflug" condition is met on both Source and Detector sides of a Sample (S).

It is noted that the Detector (D) can have, but need not have, an Aperture placed to precede it much as Aperture (AH) is configured on the Source Side in FIG. 1.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A reflectometer, ellipsometer, polarimeter or the like system comprising:
   a) a source of a beam of electromagnetic radiation;
   b) an aperture with a hole therethrough;
   c) a focusing means; and
   d) a stage for supporting a sample;

each of said aperture, focusing means and sample being oriented in identifiable planes;

such that in use said source of a beam of electromagnetic radiation is caused to direct a beam of electromagnetic radiation to a sample along an oblique angle of incidence thereto, the locus of the beam being oriented substantially perpendicular to the plane of said focusing means such that said beam passes through said focusing means and impinges upon a sample placed on said stage for supporting a sample, at an oblique angle of incidence ($\beta$) with respect to a normal to a surface of said sample, and the locus of the electromagnetic beam forms an angle ($\alpha$) with respect to a normal to the plane of said aperture;

said aperture, focusing means and stage for supporting a sample being oriented with respect to one another such that a projected plane of the aperture, a projected plane of the sample surface and a projected plane of the focusing means intersect, and such that the following condition is substantially met:

$$\text{Tan}(\alpha) = (X - f)/f \text{Tan}(\beta);$$

where "X" is the distance from the aperture, at the point at which said beam passes therethrough, to a center of said focusing means, and "f" is the focal length of said focusing means.

2. A reflectometer, ellipsometer, polarimeter or the like system as in claim 1, in which said aperture has an aspect ratio of (x/y) and is oriented such that the locus of said beam passing through said aperture is oriented at the angle ($\alpha$) with respect to the normal to the plane of said aperture;

the result being that the beam provides a spot on said sample with an aspect ratio of (x'/y') and the following condition is met:

$$(x/y) \cos(\alpha) = (x'/y') \cos(\beta).$$

3. A reflectometer, ellipsometer, polarimeter or the like system as in claim 2, in which said aperture has an aspect ratio of (x/y) and is oriented such that the spot shape on the surface of the sample is substantially of unity aspect ratio.

4. A reflectometer, ellipsometer polarimeter or the like system comprising:
   a) a source of a beam of electromagnetic radiation;
   b) an aperture with a hole therethrough;
   c) a focusing means; and
   d) a stage for supporting a sample;

each of said aperture, focusing means and sample being oriented in identifiable planes;

such that in use said source of a beam of electromagnetic radiation is caused to direct a beam of electromagnetic radiation to a sample along an oblique angle of incidence thereto, the locus of the beam being oriented substantially perpendicular to the plane of said focusing means such that said beam passes through said focusing means and impinges upon a sample placed on said stage for supporting a sample, at an oblique angle of incidence ($\beta$) with respect to a normal to a surface of said sample, and the locus of the electromagnetic beam forms an angle ($\alpha$) with respect to a normal to the plane of said aperture;

said aperture, focusing means and stage for supporting a sample being oriented with respect to one another such that a projected plane of the aperture, a projected plane of the sample surface and a projected plane of the focusing means intersect, and such that the following condition if met:

$$\text{Tan}(\alpha) = (X - f)/f \text{Tan}(\beta);$$

where "X" is the distance from the aperture, at the point at which said beam passes therethrough, to a center of said focusing means, and "f" is the focal length of said focusing means;

said ellipsometer or the like system being further characterized in that said aperture has an aspect ratio of (x/y) and is oriented such that the locus of said beam passing through said aperture is oriented at the angle (α) with respect to the normal to the plane of said aperture;

the result being that the beam provides a spot on said sample with an aspect ratio of (x'/y') and the following condition is met:

$$(x/y)\cos(\alpha)=(x'/y')\cos(\beta).$$

5. A reflectometer, ellipsometer, polarimeter or the like system as in claim 4, in which said aperture has an aspect ratio of (x/y) and is oriented such that the spot shape on the surface of the sample is substantially of unity aspect ratio.

6. A reflectometer, ellipsometer polarimeter or the like system comprising:
    a) a source of a beam of electromagnetic radiation;
    b) an aperture with a hole therethrough;
    c) a focusing means; and
    d) a stage for supporting a sample;

each of said aperture, focusing means and sample being oriented in identifiable planes;

said aperture having an aspect ratio of (x/y) and being oriented such that the locus of said beam passing through said aperture is oriented at the angle (α) with respect to the normal to the plane of said aperture;

the result being that the beam provides a spot on said sample with an aspect ratio of (x'/y') and the following condition is met:

$$(x/y)\cos(\alpha)=(x'/y')\cos(\beta).$$

7. A reflectometer, ellipsometer, polarimeter or the like system in claim 6 wherein the spot on said sample has a substantially unity aspect ratio.

8. A reflectometer, ellipsometer, polarimeter or the like system as in claim 6 in which in use said source of a beam of electromagnetic radiation is caused to direct a beam of electromagnetic radiation to a sample along an oblique angle of incidence thereto, said locus being oriented substantially perpendicular to the plane of said focusing means such that said beam passes through said focusing means and impinges upon a sample placed on said stage for supporting a sample, at an oblique angle of incidence (β) with respect to a normal to a surface of said sample, and the locus of the electromagnetic beam forms an angle (α) with respect to a normal to the plane of said aperture;

said aperture, focusing means and stage for supporting a sample being oriented with respect to one another such that a projected plane of the aperture, a projected plane of the sample surface and a projected plane of the focusing means intersect, and such that the following condition if met:

$$\operatorname{Tan}(\alpha)=(X-f)/f\operatorname{Tan}(\beta);$$

where "X" is the distance from the aperture, at the point at which said beam passes therethrough, to a center of said focusing means, and "f" is the focal length of said focusing means.

9. A reflectometer, ellipsometer, polarimeter or the like system comprising:
    a) a source of a beam of electromagnetic radiation;
    b) a stage for supporting a sample;
    c) a focusing means; and
    d) a detector or aperture/detector combination;

each of said detector, focusing means and sample being oriented in identifiable planes;

such that in use said source of a beam of electromagnetic radiation is caused to direct a beam of electromagnetic radiation to a sample placed on said stage for supporting a sample, at an oblique angle of incidence (β') with respect to a normal to a surface of said sample and reflect therefrom, the locus of said reflected beam being oriented substantially perpendicular to the plane of said focusing means such that said beam passes through said focusing means and impinges upon said detector at an angle (α') with respect to a normal thereto;

said detector, focusing means and stage for supporting a sample being oriented with respect to one another such that a projected plane of the detector, a projected plane of the sample surface and a projected plane of the focusing means intersect, and such that the following condition is substantially met:

$$\operatorname{Tan}(\alpha')=(X-f)/f\operatorname{Tan}(\beta');$$

where "X" is the distance from the detector, at the point at which said beam impinges thereupon, to a center of said focusing means, and "f" is the focal length of said focusing means.

10. A reflectometer, ellipsometer, polarimeter or the like system comprising:
    a) a source of a beam of electromagnetic radiation;
    b) an aperture with a hole therethrough;
    c) a first focusing means;
    d) a stage for supporting a sample;
    e) a second focusing means; and
    f) a detector;

each of said aperture, first focusing means and sample being oriented in identifiable planes;

such that in use said source of a beam of electromagnetic radiation is caused to direct a beam of electromagnetic radiation to a sample along an oblique angle of incidence thereto, the locus of the beam being oriented substantially perpendicular to the plane of said first focusing means such that said beam passes through said first focusing means and impinges upon a sample placed on said stage for supporting a sample, at an oblique angle of incidence (β) with respect to a normal to a surface of said sample and reflects therefrom at an angle of reflection (β'), and the locus of the incident electromagnetic beam forms an angle (α) with respect to a normal to the plane of said aperture;

said aperture, first focusing means and stage for supporting a sample being oriented with respect to one another such that a projected plane of the aperture, a projected plane of the sample surface and a projected plane of the first focusing means intersect, and such that the following condition is met:

$$\operatorname{Tan}(\alpha)=(X-f)/f\operatorname{Tan}(\beta);$$

where "X" is the distance from the aperture, at the point at which said beam passes therethrough, to a center of said first focusing means, and "f" is the focal length of said first focusing means; and each of said detector, second focusing means and sample being oriented in identifiable planes;

such that in use the locus of said reflected beam is oriented substantially perpendicular to the plane of said second focusing means such that said beam passes through said second focusing means and impinges upon said detector at an angle (α') with respect to a normal thereto;

said detector, second focusing means and stage for supporting a sample being oriented with respect to one another such that a projected plane of the detector, a projected plane of the sample surface and a projected plane of the second focusing means intersect, and such that the following condition is met:

$$\operatorname{Tan}(\alpha')=(X-f)/f\operatorname{Tan}(\beta');$$

where "X" is the distance from the detector, at the point at which said beam impinges thereupon, to a center of said second focusing means, and "f" is the focal length of said second focusing means.

11. A method of providing an oblique angle of incidence incident beam of electromagnetic radiation to a spot on a sample, wherein said beam is in focus over a substantial area of said spot comprising the steps of:
   a) providing a reflectometer, ellipsometer, polarimeter or the like system comprising:
   a) a source of a beam of electromagnetic radiation;
   b) an aperture with a hole therethrough;
   c) a focusing means; and
   d) a stage for supporting a sample;
   each of said aperture, focusing means and sample being oriented in identifiable planes;
   such that in use said source of a beam of electromagnetic radiation is caused to direct a beam of electromagnetic radiation to a sample along an oblique angle of incidence thereto, the locus of the beam being oriented substantially perpendicular to the plane of said focusing means such that said beam passes through said focusing means and impinges upon a sample placed on said stage for supporting a sample, at an oblique angle of incidence ($\beta$) with respect to a normal to a surface of said sample, and the locus of the electromagnetic beam forms an angle ($\alpha$) with respect to a normal to the plane of said aperture;
   said aperture, focusing means and stage for supporting a sample being oriented with respect to one another such that a projected plane of the aperture, a projected plane of the sample surface and a projected plane of the focusing means intersect, and such that the following condition is substantially met:

$$\mathrm{Tan}(\alpha)=(X-f)/f\,\mathrm{Tan}(\beta);$$

where "X" is the distance from the aperture, at the point at which said beam passes therethrough, to a center of said focusing means, and "f" is the focal length of said focusing means;
   b) adjusting the orientations of said aperture, focusing means and stage for supporting a sample with respect to one another such that a projected plane of the aperture, a projected plane of the sample surface and a projected plane of the focusing means intersect along a line, and such that the following condition is met:

$$\mathrm{Tan}(\alpha)=(X-f)/f\,\mathrm{Tan}(\beta).$$

12. A method as in claim 11 which further comprises using the resulting reflectometer, ellipsometer, polarimeter or the like system to acquire data by causing said source of a beam of electromagnetic radiation to provide a beam to said sample and monitoring output from said detector, and performing at least one selection from the group consisting of:
   storing at least some data provided by said data detector in machine readable media;
   analyzing at least some of the data provided by said data detector and storing at least some of the results of said analysis in machine readable media;
   displaying at least some data provided by said data detector by electronic and/or non-electronic means;
   analyzing at least some of the data provided by said data detector and displaying at least some of the results of said analysis by electronic and/or non-electronic means;
   causing at least some data provided by said data detector to produce a signal which is applied to provide a concrete and tangible result;
   analyzing at least some of the data provided by said data detector and causing at least some thereof to produce a signal which is applied to provide a concrete and tangible result.

13. A method of providing a reflected oblique angle of incidence incident beam of electromagnetic radiation from a spot on a sample, to a detector, wherein said reflected beam is in focus over a substantial area of a spot over which said beam impinges on said detector comprising the steps of:
   a) providing a reflectometer, ellipsometer, polarimeter or the like system comprising:
   a) a source of a beam of electromagnetic radiation;
   b) a stage for supporting a sample;
   c) a focusing means; and
   d) a detector;
   each of said detector, focusing means and sample being oriented in identifiable planes;
   such that in use said source of a beam of electromagnetic radiation is caused to direct a beam of electromagnetic radiation to a sample placed on said stage for supporting a sample, at an oblique angle of incidence ($\beta$) with respect to a normal to a surface of said sample and reflect therefrom, the locus of said reflected beam being oriented substantially perpendicular to the plane of said focusing means such that said beam passes through said focusing means and impinges upon said detector at an angle ($\alpha'$) with respect to a normal thereto;
   said detector, focusing means and stage for supporting a sample being oriented with respect to one another such that a projected plane of the detector, a projected plane of the sample surface and a projected plane of the focusing means intersect, and such that the following condition is substantially met:

$$\mathrm{Tan}(\alpha')=(X-f)/f\,\mathrm{Tan}(\beta');$$

where "X" is the distance from the detector, at the point at which said beam impinges thereupon, to a center of said focusing means, and "f" is the focal length of said focusing means; and
   b) adjusting the orientations of said stage for supporting a sample, said focusing means and said detector with respect to one another such that a projected plane of the detector, a projected plane of the sample surface and a projected plane of the focusing means intersect along a line, and such that the following condition is substantially met:

$$\mathrm{Tan}(\alpha)=(X-f)/f\,\mathrm{Tan}(\beta').$$

14. A method as in claim 13 which further comprises using the resulting reflectometer, ellipsometer, polarimeter or the like system to acquire data by causing said source of a beam of electromagnetic radiation to provide a beam to said sample and monitoring output from said detector, and performing at least one selection from the group consisting of:
   storing at least some data provided by said data detector in machine readable media;
   analyzing at least some of the data provided by said data detector and storing at least some of the results of said analysis in machine readable media;
   displaying at least some data provided by said data detector by electronic and/or non-electronic means;
   analyzing at least some of the data provided by said data detector and displaying at least some of the results of said analysis by electronic and/or non-electronic means;
   causing at least some data provided by said data detector to produce a signal which is applied to provide a concrete and tangible result;
   analyzing at least some of the data provided by said data detector and causing at least some thereof to produce a signal which is applied to provide a concrete and tangible result.

* * * * *